United States Patent [19]

Hasson

[11] Patent Number: 5,002,557

[45] Date of Patent: Mar. 26, 1991

[54] LAPAROSCOPIC CANNULA

[76] Inventor: Harrith M. Hasson, 2043 N. Sedgwick, Chicago, Ill. 60614

[21] Appl. No.: 334,452

[22] Filed: Apr. 6, 1989

[51] Int. Cl.⁵ .............................................. A61M 37/00
[52] U.S. Cl. ..................................... 606/191; 604/26; 604/42; 604/174
[58] Field of Search ............... 606/96, 108, 13, 14, 606/191, 119; 128/747, DIG. 26, 654; 604/49, 51, 96, 98, 178, 42, 272, 273, 274, 264, 102, 103, 283, 174, 175

[56] References Cited

U.S. PATENT DOCUMENTS

| | | |
|---|---|---|
| 3,039,468 | 6/1962 | Price . |
| 3,253,594 | 5/1966 | Matthews et al. .......... 128/DIG. 26 |
| 3,459,175 | 8/1969 | Miller . |
| 3,817,251 | 6/1974 | Hasson ............................ 604/174 X |
| 4,077,412 | 3/1978 | Moossun . |
| 4,379,458 | 4/1983 | Bauer et al. .......................... 604/264 |
| 4,535,773 | 8/1985 | Yoon ..................................... 604/51 |
| 4,540,404 | 9/1985 | Wolvek ................................. 604/96 |

Primary Examiner—Robert A. Hafer
Assistant Examiner—Kerry Owens
Attorney, Agent, or Firm—Wood, Phillips, Mason, Recktenwald & VanSanten

[57] ABSTRACT

A laparoscopic cannula is provided having a sleeve defining a hollow passageway through which a surgical instrument can be directed and having a proximal end and a distal end which projects into a cavity with the sleeve in its operative position, expandable structure at the distal end of the sleeve which is selectively expandable and collapsible and which prevents withdrawal of the sleeve in its expanded state, structure for selectively expanding and collapsing the expandable structure, a retaining collar with a tapered surface, and cooperating structure on the sleeve and collar for permitting movement of the collar relative to the sleeve towards the sleeve distal end whereby body tissue through which the sleeve is directed can be captured between the tapered collar surface and expandable structure to maintain the sleeve in its operative position.

21 Claims, 1 Drawing Sheet

# LAPAROSCOPIC CANNULA

BACKGROUND OF THE INVENTION

1. Field of the Invention

This invention relates to cannulas of the type used to perform laparoscopic surgery and, more particularly, to structure for maintaining a cannula in operative position with respect to body tissue through which the cannula extends.

2. Background Art

In performing laparoscopic surgery, an incision is made in a patient to admit a cannula which serves as a conduit for the introduction of selected surgical instruments into a body cavity. During a surgical procedure, several cannulas may be directed into the patient at spaced locations to facilitate simultaneous use of a number of instruments. The body cavity in which the operation is performed is filled with a gas to expand the surrounding tissue to create a suitably sized operating space.

In designing laparoscopic equipment, there are several objectives. First, it is important to confine the gas used to expand the cavity in which the operation is to be performed with the cannula in operative position. Deflation of the body cavity could result in interruption of a surgical procedure and/or injury to the patient's internal organs.

It is also important that the cannula be positively maintained in its operative position on the body tissue through which it passes. By positively positioning the cannulas, internal and external clashing between multiple instruments is minimized.

A further objective is to permit the cannula, in its operative position, to to be reoriented with respect to a cavity to maximize the working range for each instrument and thereby minimize the number of cannulas that must be used.

Generally, the above three objectives are competing. For example, by positively maintaining the cannula in its operative position, the leakage of gas may be minimized, however the range of motion for the instrument extending through the cannula may be limited.

Examples of prior art structures utilized to maintain a cannula in an operating position with respect to tissue through which the cannula extends are shown in each of U.S. Pat. Nos. 3,039,468, to Price; 3,253,594, to Matthews et al; 3,459,175, to Miller; and 4,077,412, to Moossun. In each of the above four patents, a disk with a large surface area is borne against one side of a tissue through which the cannula extends to thereby positively maintain the position of the cannula. The large contact area between the disks and tissue minimizes the amount of permissible repositioning of the cannula with respect to the tissue. Further, if the disk is brought sufficiently tightly against the tissue to maintain the position of the cannula, the underlying tissue may be traumatized.

There is another drawback with prior art structures utilizing an inflatable balloon/membrane to maintain the cannula in operative position. With such devices, a balloon is inflated to provide an obstruction to removal of the cannula from an incision. A tube/conduit is required to selectively inflate and deflate the balloon from a point externally of the body.

Exemplary prior art conduits are shown in U.S. Pat. Nos. 3,253,594, to Matthews et al and 3,459,175, to Miller. In each, the exposed conduit is separately passed through an incision in the body tissue. The opening for the conduits affords another escape route for gas within the cavity. The conduits are also prone to being severed or pinched. Further, the conduits are difficult to clean and potentially unsanitary when reused.

The present invention is specifically directed to overcoming the above-enumerated problems in a novel and simple manner.

SUMMARY OF THE INVENTION

According to the invention a laparoscopic cannula is provided having a sleeve defining a hollow passageway through which a surgical instrument can be directed and having a proximal end and a distal end which projects into a cavity with the sleeve in its operative position, expandable structure at the distal end of the sleeve which is selectively expandable and collapsible and which prevents withdrawal of the sleeve in its expanded state, structure for selectively expanding and collapsing the expandable structure, a retaining collar with a tapered surface, and cooperating structure on the sleeve and collar for permitting movement of the collar relative to the sleeve towards the sleeve distal end whereby body tissue through which the sleeve is directed can be captured between the tapered collar surface and expandable structure to maintain the sleeve in its operative position.

The tapered collar surface is caused to penetrate the body tissue and thereby maintain a leakproof seal around the incision. The collar does not have to be squeezed tightly against the body tissue to effect this seal and thus the possibility of local traumatization is minimized.

In a preferred form of the collar, the tapered surface thereon defines a truncated cone with the surface making an angle of preferably approximately 15° or greater with respect to the cone axis.

Further, the collar and expandable structure permit a significant amount of reorientation of the cannula in its operative position without compromising the integrity of the seal at the incision.

At the same time, the cannula is sufficiently positively maintained in its operative position so as to minimize internal and external clashing of instruments and facilitate placement in and removal of instruments from the body cavity through the cannula passageway.

Preferably, the expandable structure is a flexible membrane which surrounds the distal end of the sleeve. In a preferred form, the membrane is made from polyethylene teraphthalate which is sufficiently durable to resist rupture and positively prohibit withdrawal of the cannula from an incision. The material is nonetheless sufficiently flexible to permit significant reorientation of the cannula during an operation.

Another aspect of the invention is the provision of structure to block the passage of gas through the cannula passageway at times when there is no instrument in the cannula. In one exemplary embodiment, a hinged door is provided on the cannula and is engaged and opened by an instrument directed through the cannula passageway. Upon the instrument being withdrawn, a spring urges the door back to its closed/sealing position.

Another aspect of the invention is the formation of the sleeve in at least two parts. In a preferred form, one sleeve part defines at lest part of a conduit that is used to direct air against the membrane/balloon to effect inflation thereof and to exhaust air to collapse the membrane/balloon. The one sleeve part can be made by extrusion and preferably of plastic or fiberglass so as to be a low cost, disposable item. In a preferred form, the one sleeve part is threadably mated with a second sleeve part having the door to block the cannula passageway. The result is that the relatively expensive second part of the cannula, generally made at least in part from medical grade stainless steel, which remains externally of the patient, can be reused, whereas that part of the cannula that penetrates the patient can be disposed of and readily replaced.

The one sleeve part can be made in different lengths which can be selected depending upon the particular type of surgery and patient.

In a preferred form, the collar is designed to be removably slid over the first sleeve part and has a set screw to fix the position of the collar on the sleeve. The collar can be separated from the disposable first sleeve part and replaced on another like disposable sleeve part to cooperate with the reusable sleeve part.

In a preferred form, each of the first and second sleeve parts defines a part of the sleeve passageway.

DETAILED DESCRIPTION OF THE DRAWINGS

Figure 1:
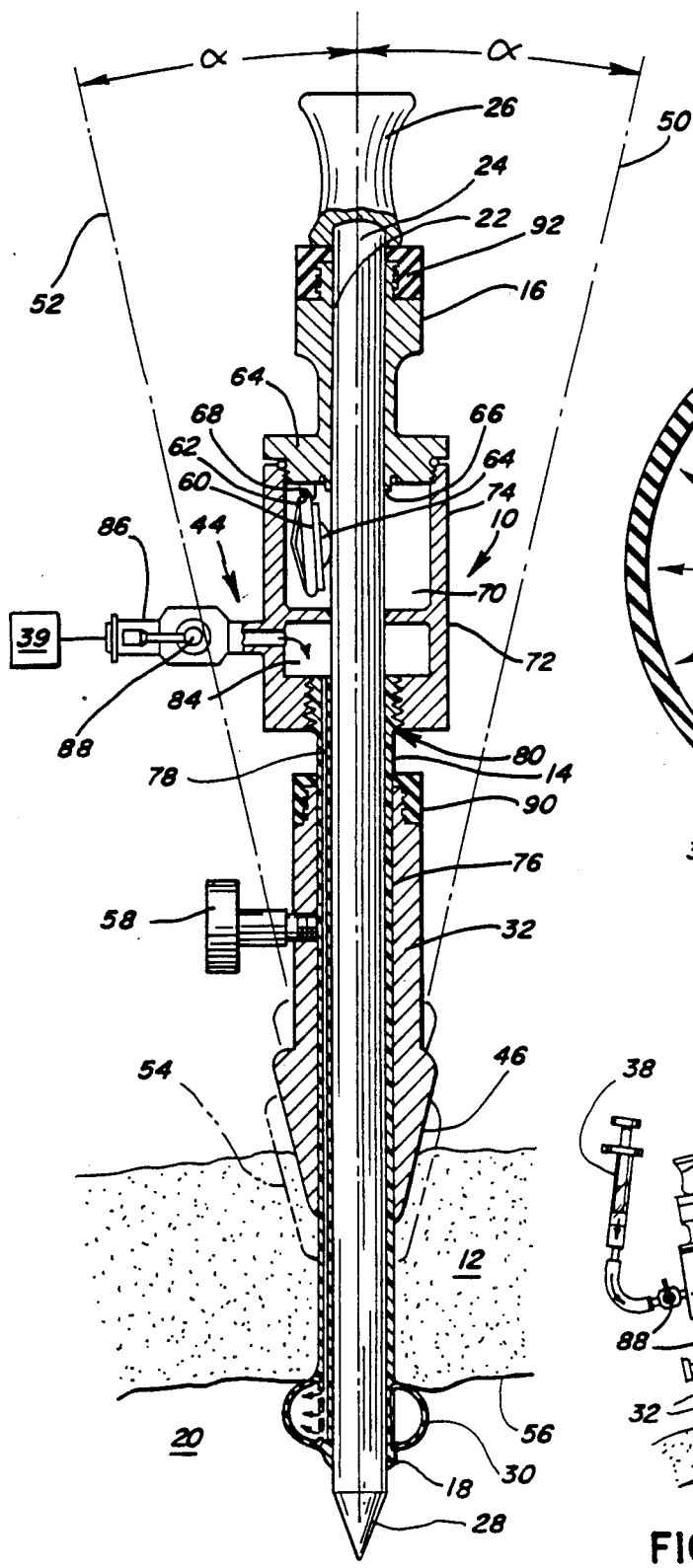
FIG. 1 is a section view of a laparoscopic cannula according to the present invention in operative position with respect to body tissue through which the cannula extends.

In FIG. 1, a preferred form of laparoscopic cannula, according to the present invention, is shown at 10 in operative position with respect to body tissue 12, as for example the abdominal wall of a patient, through which the cannula 10 extends. The cannula 10 has a sleeve 14 with a proximal end 16, which remains externally of a patient and through which the cannula 10 is manipulated, and a distal end 18, which is directed into a cavity 20 through the tissue 12. The sleeve 14 defines, a passageway 22 for communicating through the tissue 12 with the cavity 20.

To insert the sleeve 14 into the operative position of FIG. 1, a spike 24 is first directed through the sleeve passageway 22. An enlarged head 26 on the spike 24 arrests movement of the spike 24 through the cannula passageway 22 in a position wherein a sharpened end 28 of the spike 24 is exposed at the distal end 18 of the sleeve 14.

An incision (not shown) is made in the tissue 12. The sleeve 14 with the spike 24 therethrough is directed through the incision until the distal end 18 of the sleeve 14 is exposed in the body cavity 20.

To maintain the sleeve 14 in its operative position, the present invention contemplates the use of an inflatable membrane/balloon 30 at the distal end 18 of the sleeve 14 and a cooperating collar 32, surrounding the sleeve 14 and movable lengthwise relative thereto.

Figure 2:
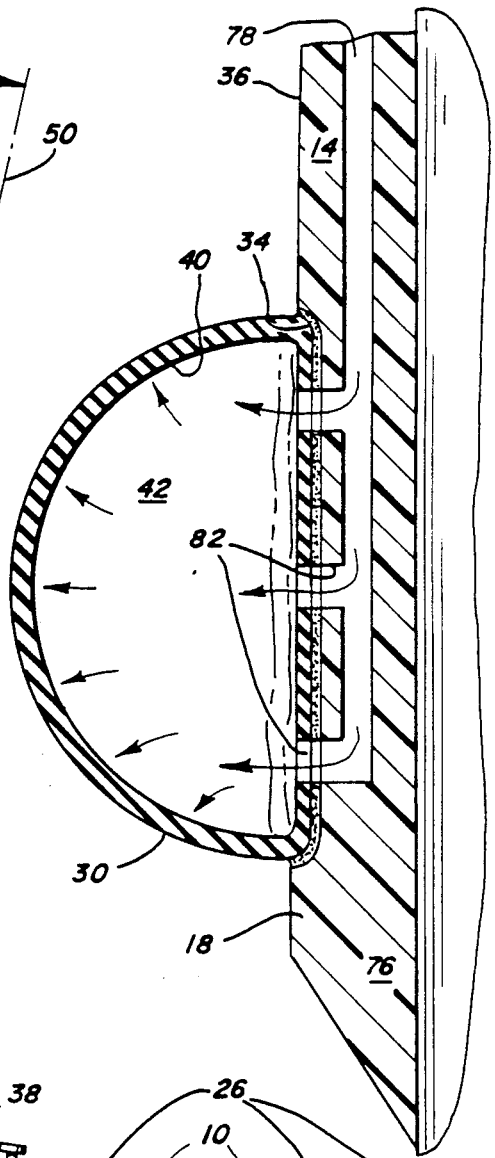
FIG. 2 is an enlarged section view of a membrane/balloon on the cannula for preventing withdrawal of the cannula from the tissue.

The details of the membrane are shown in FIG. 2. The membrane 30, which is preferably made from polyethylene teraphthalate, surrounds the distal end 18 of the sleeve 14 and resides within an annular recess 34 defined in the sleeve 14. In a collapsed state, as shown in phantom in FIG. 2, the membrane 30 has a compact profile and projects radially outwardly preferably not significantly further than the outer surface 36 of the sleeve 16. The compact storage of the membrane 30 permits the sleeve distal end 18 to be directed through the incision in the tissue 12 with minimal interference.

Once the membrane 30 is fully within the cavity 20, it can be inflated as through a syringe at 38 or through any other means, shown schematically in FIG. 1 at 39. The syringe 38 directs pressurized air or fluid radially outwardly of the sleeve 14 against the membrane surface 40. The membrane 30 is expanded sufficiently, as shown in FIGS. 1 and 2, that it prevents the sleeve 14 from being withdrawn from the tissue 12. An exemplary diameter of the expanded membrane 30 is 2.0 cm or greater, depending upon the diameter of the sleeve 14. An exemplary dimension of the expanded membrane 30 lengthwise of the sleeve 14 is 1–2 cm, again depending upon the sleeve and incision size. It is preferred to make the membrane 30 at least three times the size of the incision through which the sleeve 14 extends.

By exhausting air from the membrane chamber 42, the membrane 40 can be collapsed to facilitate withdrawal of the sleeve 14 through the incision. The details of the inflating/deflating mechanism at 44 will be described below.

The collar 32 has a tapered surface 46 which, with the membrane 30 inflated, is urged towards the membrane 30, thereby compressing the tissue 12 and capturing the tissue 12 in conjunction with the membrane 30. The collar surface 46 is shaped as a truncated cone. As seen in FIG. 1, a substantial area of tapered surface 46 is brought into contact with the tissue, thereby effecting a positive seal between the collar 32 and tissue 12.

The incline of the surface 46 is chosen so as to maximize contact area with the tissue without causing penetration thereof sufficient to contact and possibly rupture the membrane 30. In a preferred form of the invention, the angle α that the surface 46 makes with the axis of the cone is on the order of 15° or more. However, the angle may vary depending upon the thickness and nature of the tissue.

By reason of the substantial contact area between the surface 46 and tissue 12, it is possible to reorient the length of the sleeve 14 so that, for example, it is along the center lines 50, 52, without leakage, of gas from the cavity 20. If the sleeve 14 is tipped, so that it aligns with center line 50, the left side 54 of surface 46 tends to pull away from the tissue, yet not sufficiently that it disengages therefrom. Consequently, the seal remains intact entirely around the incision. The membrane 30 is sufficiently flexible to likewise conform to the inside surface 56 of the tissue 12 upon reorientation of the sleeve 14 and is sufficiently durable that it will not be prone to rupture when so deformed.

Because of the tapered configuration of the surface 46, a substantial amount of penetration can occur without traumatizing the tissue 12 around the incision. Once the collar 32 is appropriately positioned, a set screw 58 on the collar 32 can be tightened against the outer surface 36 of the sleeve 14. The sleeve 14 is thus positively maintained in the operative position of FIG. 1.

Another aspect of the invention is the provision of a door 60 to seal the passageway 22 in the absence of an instrument (not shown) or spike 24 being extended into the passageway 22. The door 60 is hingedly connected at 62 for pivoting movement relative to a radially enlarged flange 64 at the proximal end 16 of the sleeve 14. In the closed door position, a rounded projection 64 seats sealingly against a rim 66 on the flange 64. The closed door is intercepted by an instrument or the spike 24 being directed downwardly through the passageway 22 so that the door 60 is thereby pivoted to the open position in FIG. 1. Upon the instrument being removed, a spring 68 associated with the door 60 urges the door 60 back to its closed position. The door mechanism resides within a cavity 70 defined by a housing 72.

The cannula sleeve 14 is preferably defined in two parts. A first part 74 defines the passageway sealing structure including the door 60. The first sleeve part 74 remains externally of the patient at all times and is fabricated preferably mostly from medical grade stainless steel.

The second sleeve part 76 is directed through the tissue 12 and defines a conduit 78 through which the membrane 30 is selectively inflated and deflated. In a preferred form, the second sleeve part 76 is formed of plastic by extrusion. Fabrication from any other rigid material, such as fiberglass is also contemplated. The conduit 78 extending lengthwise of the sleeve part 76 can be formed in the extrusion process. The sleeve part 76 can be readily and economically manufactured so as to be disposable. It is thus possible to reuse the first part 74 and provide individually sterilized second parts 76, which are threadably connected at 80 to the first part 74. Other connections between the parts 74, 76 are also contemplated, such as bayonet, friction fit, etc.

The parts 76 can be made in a variety of lengths to be suitable for different types of operations and for different patients. By minimizing the amount of projection of the part 76 into the cavity 20, the range of movement of the instruments in the cavity 20 is maximized.

The distal end of the second sleeve part 76 is undercut, as through the use of heat, to define the recess 34 and has a plurality of radially extending outlet ports 82 in communication with the conduit 78. Inflation and deflation of the membrane 30 is accomplished through the ports 82. The conduit 78 communicates through a chamber 84 on the sleeve part 74 with a conduit 86 integrally formed with the sleeve housing 72. The conduit 86 has a shut-off and/or one-way valve 88, which can be operated to prevent escape of air or fluid from the membrane chamber 42 with the membrane 40 inflated.

To place the cannula 10 in its operative position, the membrane 30 is deflated to the phantom position in FIG. 2. The spike 24 is directed through the cannula passageway 22 so that the spike end 28 projects from the distal end 18 of the sleeve 14. The spike 28 and surrounding sleeve are then directed through an incision in the tissue 12 until the recess 34 is entirely within the cavity 20. A valve 88 is opened and the syringe 38 or other pressurized air source is operated to inflate the membrane 30. Once the membrane 30 is fully inflated, the shut-off valve 88 can be closed to confine the air or fluid in the membrane 30. The spike 24 can then be removed from the sleeve 24 whereupon the door 60 closes to seal the passageway 22. The collar 32 is then urged towards the membrane 30, thereby compressibly capturing the tissue 12 in conjunction with the membrane 30. The set screw 58 is tightened to fix the location of the collar 32 and thereby maintain the cannula 10 in its operative position so that a desired instrument can be directed through the passageway 22 into the cavity 20.

To prevent escape of gas from the cavity 20 between the collar 32 and sleeve 14, a gasket 90 is provided on the end of the collar 32. A similar gasket 92 is provided at the proximal end 16 of the sleeve to sealingly cooperate with an instrument extended through the passageway 22.

Figure 3:
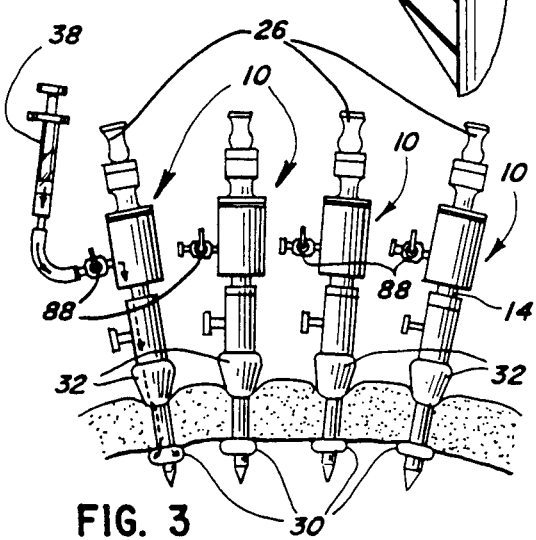
FIG. 3 is a section view of a piece of tissue with several cannulas according to the present invention extended through the tissue and each in operative position.

FIG. 3 shows an arrangement of several of the cannulas 10 which may be simultaneously utilized during an operation. Relative orientations of the cannula 10 are fixed sufficiently that internal and external clashing between the cannulas 10 and any instruments extended through the sleeve 14 thereon is minimized.

The foregoing disclosure of specific embodiments is intended to be illustrative of the broad concepts comprehended by the invention.

I claim:

1. A cannula for extension through tissue into a cavity, said cannula comprising:
   a cylindrical sleeve defining a hollow passageway through which a surgical instrument can be directed,
   said sleeve having (a) a proximal end to be manipulated by a user in directing the sleeve into its operative position through body tissue into a body cavity, (b) a distal end which projects into a cavity with the sleeve in its operative position, and (c) a cylindrical outer surface;
   expandable means at the distal end of the sleeve for preventing withdrawal of the sleeve from a tissue with said expandable means in an expanded state,
   said sleeve having a radial recess,
   said expandable means being collapsible from its expanded state wherein it projects radially sufficiently to prevent passage through an incision to a collapsed state in which the expandable means projects radially not significantly further than the outer surface of the sleeve so as not to prevent passage of the distal sleeve end into and out of an incision in body tissue;
   means for selectively placing said expandable means in the expanded and collapsed states;
   a retaining collar having a tapered surface; and
   cooperating means on the sleeve and collar for permitting movement of the collar relative to the sleeve towards the sleeve distal end whereby body tissue through which the sleeve is directed can be captured between the tapered collar surface and the expandable means to thereby maintain the sleeve in its operative position.

2. The cannula according to claim 1 wherein said tapered surface is conical and diminishes in diameter from the proximal end towards the distal end of the sleeve.

3. The cannula according to claim 1 wherein said expandable means comprises an expandable membrane which surrounds the distal end of the sleeve.

4. The cannula according to claim 1 wherein means are provided on the collar for fixing the position of the collar at a desired location on the sleeve.

5. The cannula according to claim 1 wherein means are provided for selectively closing the sleeve passageway to prevent passage of gas through the sleeve from the distal end to the proximal end thereof.

6. The cannula according to claim 1 wherein said collar tapered surface defines a truncated cone.

7. The cannula according to claim 2 wherein said sleeve distal end has an outer cylindrical surface and the collar surface tapers to a diameter only slightly larger than the diameter of the sleeve cylindrical surface.

8. The cannula according to claim 3 wherein said sleeve has a cylindrical wall and said means for selectively placing said expandable means in the expanded and collapsed states comprises a conduit having one end in communication with a surface of said membrane and an opposite end through which air can be selectively (a) directed in and through the conduit to act against the membrane surface to thereby place the membrane in its expanded state and (b) exhausted from the conduit to place the membrane in its collapsed state, said conduit being integrally formed within the cylindrical conduit wall.

9. The cannula according to claim 3 wherein said membrane is made from polyethylene teraphthalate.

10. The cannula according to claim 7 wherein the tapered surface makes an angle of approximately 15° central axis of the cone.

11. The cannula according to claim 8 wherein means are provided on a first sleeve part for selectively blocking the sleeve passageway to prevent passage of gas through the sleeve from the distal end to the proximal end thereof, said conduit is provided in a second sleeve part and means are provided for releasably joining said first and second sleeve parts.

12. The cannula according to claim 11 wherein each said first and second sleeve part defines part of said sleeve passageway.

13. The cannula according to claim 12 wherein said second sleeve part is defined by extrusion forming.

14. The cannula according to claim 12 wherein said second part is defined by extruded plastic.

15. The cannula according to claim 12 wherein said means for releasably joining comprises cooperating threads on said first and second sleeve parts.

16. A cannula for extension through tissue into a cavity, said cannula comprising:
   a sleeve defining a hollow passageway through which a surgical instrument can be directed;
   said sleeve having (a) proximal end to be manipulated by a user in directing the sleeve into an operative position through body tissue into a body cavity and (b) a distal end which projects into a cavity with the sleeve in its operative position,
   said sleeve having first and second joinable parts;
   means on the second sleeve part for preventing withdrawal of the sleeve from body tissue through which the cannula extends,
   said preventing means comprises a membrane that is radially expandable from a collapsed state to an expanded state,
   said sleeve having a recess for reception of the membrane in its collapsed state; and
   means on the sleeve for cooperating with the preventing means to capture body tissue through which the sleeve extends to thereby maintain the sleeve in its operative position.

17. The cannula according to claim 16 wherein said first and second sleeve parts are threadably engaged with each other.

18. The cannula according to claim 16 wherein said second sleeve part has a cylindrical wall that is extrusion formed to define a conduit integrally within said wall through which the membrane can be selectively inflated to an expanded state and deflated to a collapsed state.

19. The cannula according to claim 18 wherein means are provided on said first sleeve part for selectively closing the sleeve passageway to prevent passage of gas through the sleeve passageway between the distal and proximal ends.

20. A cannula for extension through tissue into a cavity, said cannula comprising:
   a sleeve defining a hollow passageway through which a surgical instrument can be directed,
   said sleeve having (a) a proximal end to be manipulated by a user in directing the sleeve into an operative position through body tissue into a cavity and (b) a distal end which projects into a cavity with the sleeve in its operative position,
   said sleeve having first and second joinable parts;
   means on the second sleeve part for preventing withdrawal of the sleeve from body tissue through which the cannula extends; and
   means on the sleeve for cooperating with the preventing means to capture body tissue through which the sleeve extends to thereby maintain the sleeve in its operative position,
   wherein the cooperating and preventing means on the sleeve comprises a slidable collar having a tapered surface for bearing against body tissue and cooperating with the preventing means on the second part to capture body tissue in conjunction therewith.

21. The cannula according to claim 20 wherein cooperating means are provided on said sleeve and collar for permitting separation of said collar from the sleeve.

* * * * *